US009463069B2

(12) United States Patent
Dunworth et al.

(10) Patent No.: US 9,463,069 B2
(45) Date of Patent: Oct. 11, 2016

(54) AUTOMATED WORK STATION FOR POINT-OF-CARE CELL AND BIOLOGICAL FLUID PROCESSING

(71) Applicant: SpineSmith Partners, L.P., Austin, TX (US)

(72) Inventors: Kevin Dunworth, Austin, TX (US); Matthew Murphy, Austin, TX (US); Katy Moncivais, Austin, TX (US); Michelle Kelly, Austin, TX (US); Jessica Terrazas, Austin, TX (US); Theodore Sand, Austin, TX (US); Joshua K. Hoyt, Portland, OR (US); Greg Hinzmann, Beaverton, OR (US); Paul DeKoning, Portland, OR (US); David John Sayler, Portland, OR (US); Bartley Johnson, West Linn, OR (US)

(73) Assignee: SpineSmith Partners, L.P., Austin, TX (US)

( * ) Notice: Subject to any disclaimer, the term of this patent is extended or adjusted under 35 U.S.C. 154(b) by 0 days.

(21) Appl. No.: 14/061,597

(22) Filed: Oct. 23, 2013

(65) Prior Publication Data

US 2014/0110913 A1 Apr. 24, 2014

Related U.S. Application Data

(60) Provisional application No. 61/717,418, filed on Oct. 23, 2012, provisional application No. 61/803,399, filed on Mar. 19, 2013.

(51) Int. Cl.
*B62B 3/02* (2006.01)
*A61B 19/02* (2006.01)

(52) U.S. Cl.
CPC ............ *A61B 19/0248* (2013.01); *A61B 50/10* (2016.02); *A61B 50/13* (2016.02); *A61B 50/30* (2016.02); *A61B 2560/0437* (2013.01)

(58) Field of Classification Search
CPC ...................................................... B62B 3/1408
USPC ....................... 280/47.34, 47.35, 79.11, 79.3
See application file for complete search history.

(56) References Cited

U.S. PATENT DOCUMENTS

| D296,143 | S | * | 6/1988 | Bettess | D34/21 |
|---|---|---|---|---|---|
| 4,976,450 | A | * | 12/1990 | Ellefson | 280/79.11 |
| 5,634,649 | A | * | 6/1997 | Breining et al. | 280/47.35 |
| D387,168 | S | * | 12/1997 | Edelman et al. | D24/186 |
| D389,917 | S | * | 1/1998 | Hornback et al. | D24/186 |
| 5,887,878 | A | * | 3/1999 | Tisbo et al. | 280/47.19 |
| 6,170,839 | B1 | * | 1/2001 | Kizewski | 280/47.26 |
| D438,952 | S | * | 3/2001 | Cimino et al. | D24/107 |
| 6,339,732 | B1 | * | 1/2002 | Phoon et al. | 700/237 |
| D459,477 | S | * | 6/2002 | Stocks et al. | D24/164 |
| D465,895 | S | * | 11/2002 | Pfefferle et al. | D34/19 |
| 6,493,220 | B1 | * | 12/2002 | Clark et al. | 361/679.41 |

(Continued)

*Primary Examiner* — Jeffrey J Restifo
(74) *Attorney, Agent, or Firm* — Winstead PC

(57) ABSTRACT

The invention is directed to a work station for use in performing processing of patient samples, storing equipment and drugs in a hospital and the like, the cart having a lower housing having caster wheels mounted on the bottom thereof, the lower housing having angular-shaped side panels therearound which may be opened for entrance into all sides of the housing, and one or more of the side panels; an upper housing mounted on top of the lower housing, the upper housing having one or more side panels therearound; and one or more work areas mounted on top of the upper housing, the shelf adapted for receiving point-of-care equipment.

6 Claims, 2 Drawing Sheets

(56) References Cited

U.S. PATENT DOCUMENTS

| | | | |
|---|---|---|---|
| D477,082 S * | 7/2003 | Bromley | D24/170 |
| D477,083 S * | 7/2003 | Bromley | D24/170 |
| 6,626,445 B2 * | 9/2003 | Murphy et al. | 280/47.34 |
| D486,915 S * | 2/2004 | Warschewske et al. | D24/185 |
| 6,722,673 B1 * | 4/2004 | Hamlin | 280/47.35 |
| 7,009,840 B2 * | 3/2006 | Clark et al. | 361/679.41 |
| 7,198,511 B2 * | 4/2007 | Brennan, Jr. | 439/501 |
| 7,338,055 B2 * | 3/2008 | Fuentes | 280/79.3 |
| 7,490,837 B2 * | 2/2009 | Pond et al. | 280/47.35 |
| 7,612,999 B2 * | 11/2009 | Clark et al. | 361/679.4 |
| 7,621,544 B2 * | 11/2009 | Rossini | 280/79.3 |
| 7,789,403 B2 * | 9/2010 | Wilsher | 280/79.3 |
| 7,791,866 B2 * | 9/2010 | Clark et al. | 361/679.01 |
| 7,990,691 B2 * | 8/2011 | Clark et al. | 361/679.01 |
| 8,157,337 B2 * | 4/2012 | Manalang et al. | 312/249.8 |
| 8,172,242 B1 * | 5/2012 | Crandall | 280/47.35 |
| 8,215,650 B2 * | 7/2012 | Arceta et al. | 280/47.35 |
| 8,286,977 B2 * | 10/2012 | Butler et al. | 280/47.35 |
| 8,322,732 B2 * | 12/2012 | McKay et al. | 280/47.35 |
| 8,360,446 B1 * | 1/2013 | Hertan | 280/47.35 |
| 8,526,176 B2 * | 9/2013 | Clark et al. | 361/679.41 |
| 8,662,605 B2 * | 3/2014 | McRorie et al. | 312/276 |
| 8,708,352 B2 * | 4/2014 | Quirico et al. | 280/47.35 |
| 2002/0165641 A1 * | 11/2002 | Manalang et al. | 700/237 |
| 2004/0186357 A1 * | 9/2004 | Soderberg et al. | 600/300 |
| 2005/0275178 A1 * | 12/2005 | Huesdash et al. | 280/47.35 |
| 2007/0001413 A1 * | 1/2007 | Rossini | 280/47.35 |
| 2007/0228680 A1 * | 10/2007 | Reppert et al. | 280/47.35 |
| 2008/0084147 A1 * | 4/2008 | Brown | 312/223.3 |
| 2008/0281167 A1 * | 11/2008 | Soderberg et al. | 600/300 |
| 2009/0221880 A1 * | 9/2009 | Soderberg et al. | 600/300 |
| 2010/0213679 A1 * | 8/2010 | Smith et al. | 280/47.35 |
| 2011/0025007 A1 * | 2/2011 | Butler et al. | 280/47.35 |
| 2011/0042911 A1 * | 2/2011 | Kozlowski et al. | 280/47.35 |
| 2014/0084558 A1 * | 3/2014 | Ergun et al. | 280/47.35 |

* cited by examiner

AUTOMATED WORK STATION FOR POINT-OF-CARE CELL AND BIOLOGICAL FLUID PROCESSING

CROSS-REFERENCES TO RELATED APPLICATIONS

This Application claims the benefit under 35 U.S.C. §119(e) of U.S. Provisional Patent Application No. 61/717,418 filed Oct. 23, 2012, and U.S. Provisional Patent Application No. 61/803,399 filed Mar. 19, 2013, each of which is incorporated herein by reference in its entirety as if fully set forth herein.

BACKGROUND OF THE INVENTION

There is a need to provide mobile, compact, but multi-functional carts for use at point-of-care in a therapeutic setting (e.g., hospital surgical suites, surgical center, pain management center, etc.). There also is a need to be able to remotely control instrumentation that is not compatible with the instrumentation being present in a critical care setting, such as an operating room. The lack of this type of multi-functional cart hampers the processing of samples taken from patients; samples which need to be processed under strict regulation and control. Ideally, in one embodiment such a multi-functional cart would support sample ID tracking (i.e., bar coding option), have a work surface for sample processing, is able to display in real time the status of instrumentation remote to the location of the work station, is able remotely to control and schedule the instrumentation, has two-way communication capability, has an inventory tracking function, can issue reports to various recipients (e.g., the attending surgeon), among other features to support the functioning of the instrumentation and the process provided at point-of-care. In another embodiment, the multi-functional cart would itself house instrumentation to process patient samples, as well as the other features and capabilities already described above. In another embodiment, the multi-functional cart would itself house instrumentation to perform on-site analysis of the patient samples in near-real or real time, the results of which would be processed, computed, recorded and reported by the other capabilities of the multi-functional cart without further manual manipulation.

Separating cells of interest out of patient samples and their biological fluids has been performed for many years, and usually is based on the application of centrifugation. For processing systems to be of use in providing cellular therapy at point of care, the processing technology should be sterilizable and a "closed system", which means that there is no exposure of the biological fluid and the separated cell components to adventitious agents. Other factors that determine the utility of such a processing system is the composition of the cell preparation, the viability of the cells of interest and the volume in which the cells are collected. Another requirement for such technology is to provide for the facile handling of various types of biological fluids, ranging from bone marrow aspirate, whole blood, fluid obtained from subcutaneous tissue depots, among other fluids of biological origin. One of the objectives of handling such biological fluids is to provide for concentration of cell-free subcomponents of such biological fluids.

There are no known technology platforms that embody all of the technical innovations of the disclosed invention. There are examples of integrated processing systems that can process some of the biological fluids contemplated in this disclosure, but not all such relevant fluids. For example, the Cellution Instrument (Cytori, San Diego, Calif.) is portrayed as being capable of performing enzymatic digestion of adipose tissue to produce a cell preparation. Another system, Syngen-1000 (Synergenesis, Sacramento, Calif.) is designed to concentrate cells from cord blood, bone marrow aspirate and lipoaspirate fluid. However, the Syngen-1000 doesn't have the capability to concentrate biological fluids like platelet poor plasma (PPP) to produce a concentrated fluid with elevated levels of proteins like fibrinogen. There are no such systems available in the marketplace that serve the functions of a work station as well as accommodating the sample processing technology for producing therapeutically beneficial autologous cell and biological fluid preparations for use at point-of-care.

The claimed invention sets forth an automated workstation that fulfills all of these requirements, thereby facilitating the processing of patient samples in full compliance with facility and other regulations applicable for dealing with patients in a medical setting.

SUMMARY OF THE INVENTION

An embodiment of the invention is directed to a work station for use in performing processing of patient samples, storing equipment and drugs in a hospital and the like, the cart comprising: a lower housing having caster wheels mounted on the bottom thereof, the lower housing having angular-shaped side panels therearound which may be opened for entrance into all sides of the housing, and one or more of the side panels; an upper housing mounted on top of the lower housing, the upper housing having one or more side panels therearound; and one or more work areas mounted on top of the upper housing, the shelf adapted for receiving point-of-care equipment.

In another embodiment, the inventive work station includes an instrument, like a centrifuge, which is capable of processing patient samples, another instrument for processing biological fluids to concentrate the fluids, the cart comprising: a lower housing having caster wheels mounted on the bottom thereof, the lower housing being of a dimension and depth to accommodate a centrifuge and related means to move fluids (via syringe or pump) from the disposable device spun in the centrifuge to other processing instrumentation; an upper housing mounted on top of the lower housing, the upper housing accommodating the sample analysis instrumentation, work surfaces, data recording, two-way communications, a user interface (UI) and computer capability.

An important benefit of the inventive work station is that the features and functions of the work station are directed toward performing processes that enable the physician to customize the practice of medicine on an individual patient basis.

DETAILED DESCRIPTION OF EXEMPLARY EMBODIMENTS

Figure 1:
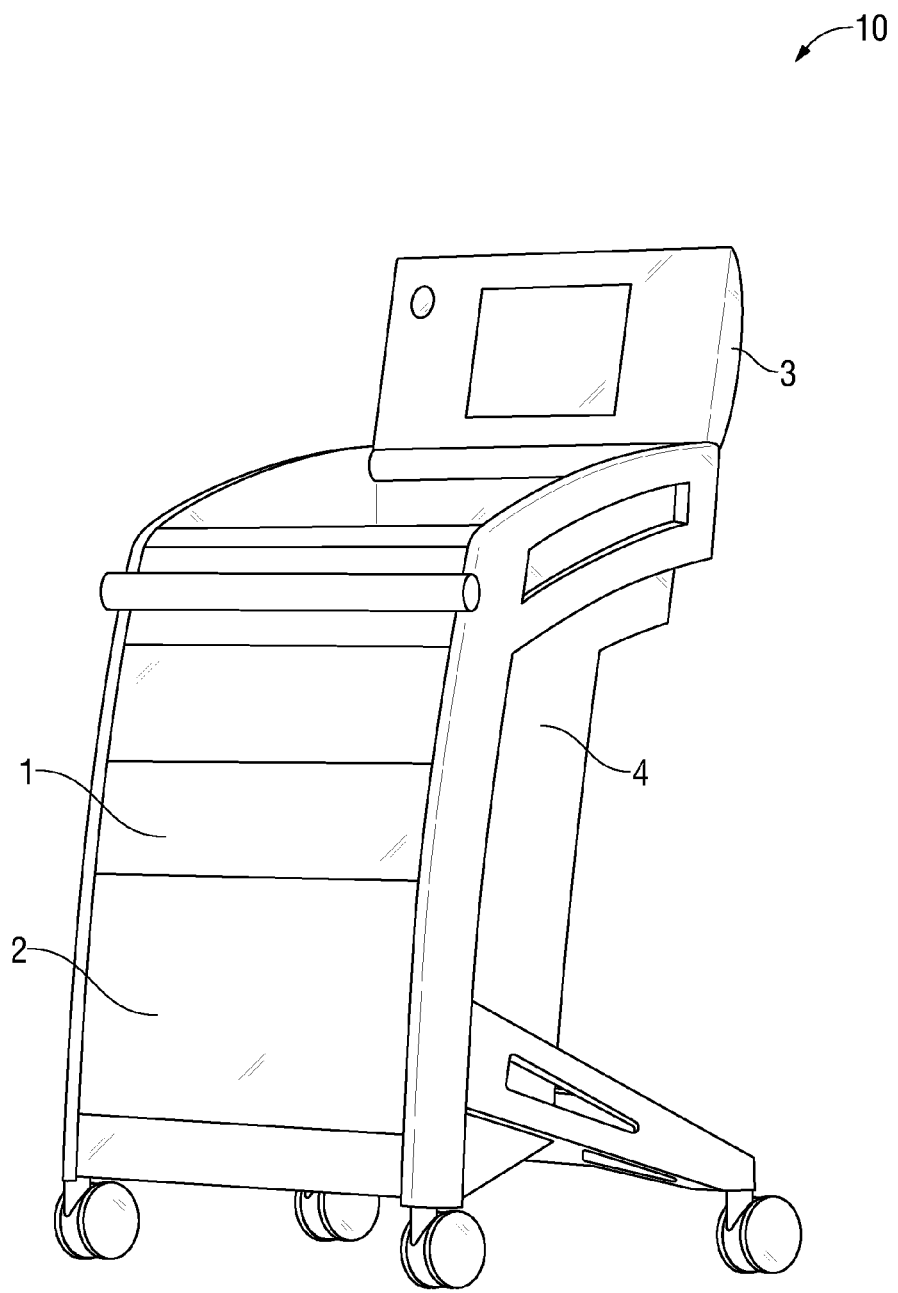
FIG. 1 shows a work station in accordance with an embodiment of the invention.

There are a number of critical features that are missing from the available commercialized carts that make them inadequate and incapable of performing the functions of the claimed invention.

One embodiment of the claimed invention provides a number of features, such as storage bins or electrical charging stations, already found on existing medically-oriented carts. Additionally, the inventive work station enables processing of patient-derived materials in a manner that is fully compliant with all FDA, HIPPA and hospital standards for ensuring the safety and privacy of the patient health information of the patient being treated.

An embodiment of the invention provides a computer interface and a user interface that is tailored to control all aspects of the processing of patient-derived materials, including remote control of instruments that are needed during the processing, logging and tracking of patient health information, recording of lot numbers of materials used during the process, status updates on the instrumentation, billing and inventory control will be accomplished by a two-way communications capability, and the issuance of reports to individuals remote to the "point-of-care" (POC) site or to persons who will review the reports at a later time than during the POC procedure. The ability to issue reports incorporating information gathered from procedures controlled by and performed at the inventive work station is a point of novelty of the claimed invention.

In order to provide controlled and safe procedures when working with patient-derived materials at POC, it is necessary to support a number of disparate functions and capabilities, including data entry, remote control and monitoring of instrumentation, creation of reports, providing a work surface, storage of critical components, bar coding and two-way communication capabilities. The primary function of the work station is to facilitate the processing of patient-derived materials. Consequently, in one embodiment, the work station will incorporate appropriate features and capabilities as follows: a work-surface tailored to patient-derived materials handling and processing; a work-surface that slides to expose tools to facilitate processing when needed, but can slide back and be locked to protect these tools when not in use; storage options tailored to the processing; a computer interface that controls key functions (remotely programs, monitors and provides real-time status updates on instrumentation present elsewhere in the facility, and the charging status of any devices needed during the processing, among other functions); a user interface based on the computer and communications capability of the Work Station that securely can record data (i.e., Operator ID, date/time, location, procedure, barcoded information specific to the patient and the procedure, including identification of instrumentation and other components used during the process); communications capability for 2-way remote interaction (physician with remotely-located expert, medical personnel at POC with remotely-located expert); the capability to provide data for procedure billing, procedure-related data (i.e., lot numbers for inventory control), and patient material-dependent outcomes (i.e., if bone marrow aspirate is part of the procedure, then total nucleated cells obtained and their viability, among other parameters).

In addition to the foregoing features, capabilities and functionality of the inventive work station, the work station will also provide personnel at POC with access to background information on the procedures to be performed, technical videos and other patient- or procedure-dependent supporting information.

FIG. 1 shows a conceptual rendering of an embodiment of the inventive work station described herein, showing some of the features and capabilities of the work station. The work station 10 contains a storage space 1 for the storage disposable items such as gloves and syringes. The work station 10 also contains space 2 that is capable of holding one or more charging station(s) for electrical and electronic devices. Each of spaces 1 and 2 contains side panels 4. The workstation also contains a touchscreen computer with user interface 3 for integrated control of remote instrumentation. The touch screen 3 can be closed to provide a work surface for the handling and processing of patient-derived materials.

In certain embodiments, the space 2 of work station 10 comprises a work surface that slides to expose a space for the storage of tools. The touch screen computer 3 allows the point-of-care personnel to perform secure exchange of patient data and information regarding the procedures to be performed.

Figure 2:
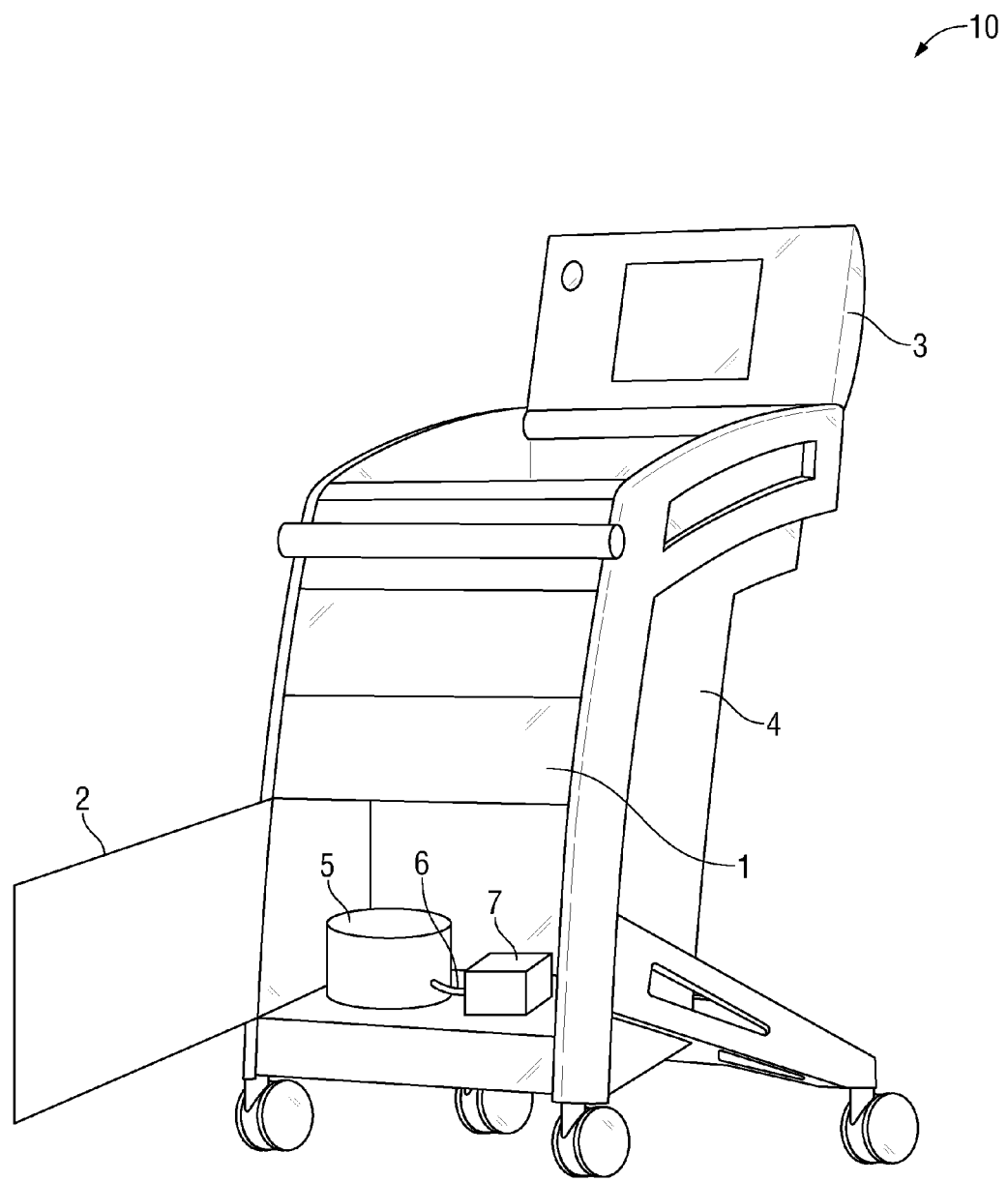
FIG. 2 shows a work station in accordance with an embodiment of the invention.

FIG. 2 shows a conceptual rendering of an embodiment of the inventive work station 10. In another embodiment, the inventive work station 10 includes the physical means of processing the patient samples within the housing of the work station. The work station is of a dimension to accommodate a centrifuge 5, fluid handling tubing, 6, and syringes and pumps 7. The instrumentation disclosed herein consists of a portable platform element of the work station, which houses one or more centrifuges 5 that are controlled by the UI of the work station 10 and which communicate with an interactive onboard computer. The associated sterile, disposable device that will receive the patient's sample will be capable of handling a variety of biological fluids, including fluid-only fluid obtained from a subcutaneous adipose tissue depot, lipoaspirate fluid, bone marrow aspirate, and blood. The processing of the patient's samples will be determined and programmed at the UI and not at the centrifuge 5 itself. The output concentrated patient cell preparation and by-products of the processing sequence will be moved to appropriate secondary collection containers or additional instrumentation with or without manual intervention. In one embodiment, bone marrow aspirate will be processed yielding a concentrated cell preparation and a substantially cell free fluid referred to as "platelet poor plasma (PPP)". The concentrated cell preparation can be mixed with the PPP or can be mixed with PPP that has been separately concentrated in a fiber-containing device in fluid communication with the original separation device. The fiber-containing device is capable of concentrating a variety of components found in plasma, including, but not limited to fibrinogen, prothrombin, fibronectin, alpha-2-macroglobulin, VEGF, PDGF and other growth factors and proteins.

In another embodiment, the patient sample will be placed directly in a fiber-containing device and the biological fluid will be reduced in volume by passing the cell-containing fluid back and forth through the lumen of the fibers. Water, ions and some biological components will pass through the pores of the fibers, while larger biological components, including proteins, growth factors and cell particles (e.g., white blood cells, red blood cells, platelets, monocytes and neutrophils, among others) will remain inside the luminal space of the fibers and once the volume has been reduced, the concentrated biological fluid can be recovered for therapeutic use. The use of direct volume reduction without the use of the centrifugal instrumentation is especially suited to the processing of biological preparations with reduced levels of red blood cells, including lipoaspirate fluid, fluid-only fluid from adipose depots and biological samples already processed in the centrifugal portion of the work station's instrumentation.

WORKING EXAMPLES

Example 1

The work station is placed adjacent to or in the treatment room or operating room in such a way that it can remain stationary for the duration of the processing event. The sequence for processing a patient's sample is initiated by the operator entering the appropriate user name and password in order to gain access to the User Interface features and functions. Depending on the nature of the procedure the operator will enter critical information, either on a virtual keyboard or via bar code entry or by both means. Critical information will include sufficient patient health information so as to allow for billing and report generation to be completed, while maintaining confidentiality and the privacy of the patient. Once the processing sequence details have been initiated, the operator supports the collection of the patient's sample. For example, a bone marrow aspiration kit will be transferred to the sterile field or other appropriate physical location near the patient. Once the patient's sample has been collected and loaded into the appropriate sterile, single-use disposable device, the operator places the device in the centrifuge and initiates a centrifugation cycle. If the centrifuge is remote to the work station, the operator will remove the device from the treatment area and place the device in the remotely located centrifugation system. The centrifuge cycle will be initiated and the operator can return to the work station to perform additional processing and support activities. Cycle progress will be monitored on the UI output screens, so the operator need not leave the patient treatment area if the sample is being processed remotely, until the cycle is completed. If remotely processed, the operator will recover the cycled device and any secondary containers of the patient's therapeutic preparations and return to the work station. Additional processing of the patient's preparations can be performed at the work station, including concentrating PPP or other processing contemplated with the fiber-containing device. Once the final therapeutic cell-containing or biological fluid-containing therapeutic preparation has been obtained, the preparation is transferred under direction of the physician in a manner so as to enable treatment of the patient. If requested by the physician, the operator can analyze a small retained volume of the patient's sample and/or the concentrated therapeutic preparation for the number of nucleated cells, the viability of the cells present and other parameters appropriate to the sample analysis instrumentation that is located within the work station housing. Report generation will be initiated at the completion of all support/processing activities, including an inventory report to be transmitted to a central location for inventory monitoring, and a sample analysis report to be provided to a central location, as well as being provided to the physician, his staff or other designated recipient. Storage and transmittal of pertinent patient health information will be fully compliant with all applicable standards, including those required to meet HIPPA and FDA standards for privacy.

Example 2

The work station is placed adjacent to or in the treatment room or operating room in such a way that it can remain stationary for the duration of the processing event. The sequence for processing a patient's sample is initiated by the operator entering the appropriate user name and password in order to gain access to the User Interface features and functions. Depending on the nature of the procedure the operator will enter critical information, either on a virtual keyboard or via bar code entry or by both means. Critical information will include sufficient patient health information so as to allow for billing and report generation to be completed, while maintaining confidentiality and the privacy of the patient. Once the processing sequence details have been initiated, the operator supports the collection of the patient's sample. For example, the tools and instrumentation (e.g., canulea) for performing fluid-only sample collection will be transferred to the sterile field or other appropriate physical location near the patient. Once the patient's sample has been collected and loaded into the appropriate sterile, single-use fiber-containing device it is inserted into the processing platform on the work station in order to reduce the volume of the sample. Volume reduction can be obtained by activating a manual processing sequence involving the passage of fluid through the lumen of the fibers in the device via attached syringes, or an automated sequence involving pneumatic motion of the syringes can be utilized. Water, ions and some biological materials will pass through the pores of the fibers, while cells, including white blood cells, red blood cells, platelets, neutrophils, mononuclear cells and progenitor cells, along with biologically relevant proteins and growth factors will be retained with the lumen of the fibers. Once volume reduction of the patient's sample has been achieved, the luminal compartment is accessed to recover the patient's therapeutic biological preparation. Once the final therapeutic cell-containing or biological fluid-containing therapeutic preparation has been obtained, the preparation is transferred under direction of the physician in a manner so as to enable treatment of the patient. If requested by the physician, the operator can analyze a small retained volume of the concentrated therapeutic preparation for the number of nucleated cells, the viability of the cells present and other parameters appropriate to the sample analysis instrumentation that is located within the work station housing. Report generation will be initiated at the completion of all support/processing activities, including an inventory report to be transmitted to a central location for inventory monitoring, and a sample analysis report to be provided to a central location, as well as being provided to the physician, his staff or other designated recipient. Storage and transmittal of pertinent patient health information will be fully compliant with all applicable standards, including those required to meet HIPPA and FDA standards for privacy.

Results of the cell concentration and viability of fluid-only patient samples after processing in a fiber-containing device is shown in Table 1. The cell analysis was performed with a NucleoCounter (Chemometec, Inc.) and consists of two cartridges loading with a small aliquot of the cell preparation, either before processing or after processing. As indicated, the change in viability of the samples processed in the fiber-containing device was less than 10%, indicating that the physical process of flow through the lumen of the fibers did not cause a substantial change in viability, despite the shear forces being experienced by the cells as they flow through the fibers. Table 1 shows the total nucleated cell (TNC) concentration in bone marrow aspirate (BMA) and bone marrow concentrate (BMC) after processing in a disposable device and centrifuge system with corresponding fold increase over BMA and viability at 24 hour analysis time point.

TABLE 1

| Sample | BMA (TNC/mL) | BMC (TNC/mL) | Fold Increase | % Viability |
|---|---|---|---|---|
| 1 | $2.53 \times 10^7$ | $1.18 \times 10^8$ | 4.7 | 98.8% |
| 2 | $3.13 \times 10^7$ | $8.49 \times 10^7$ | 2.7 | 98.5% |
| 3 | $1.96 \times 10^7$ | $1.16 \times 10^8$ | 5.9 | 99.7% |

In the preceding detailed description, the invention is described with reference to specific exemplary embodiments thereof and locations of use within the spine. Various modifications and changes may be made thereto without departing from the broader spirit and scope of the invention as set forth in the claims. The specification and drawings are, accordingly, to be regarded in an illustrative rather than a restrictive sense.

What is claimed is:

1. A work station for use in performing processing of patient samples, storing equipment and drugs in a medical setting, the cart comprising:

a lower housing having caster wheels mounted on the bottom thereof, the lower housing having angular-shaped side panels therearound which may be opened for entrance into all sides of the lower housing, and one or more of the side panels;

an upper housing mounted on top of the lower housing, the upper housing having one or more side panels therearound;

angular-shaped side panels disposed on each side of the work station to permit entrance into the work station from each side of the work station;

a portable platform element disposed within the upper housing that is adapted to house one or more centrifuges;

a centrifuge disposed upon the portable platform element, the centrifuge adapted to receive and spin a disposable device to separate fluids within the disposable device;

a pump coupled to the centrifuge via fluid handling tubing to remove the fluids from the disposable device;

one or more work areas mounted on top of the upper housing, the shelf adapted for receiving point-of-care equipment;

an electronic capability that permits control of remotely located equipment necessary to the processing of the patient sample; and a touch screen computer that is integrated with the work station and adapted to control the centrifuge to process the patient samples and record results of the processed patient samples.

2. The work station of claim 1 further comprising a work surface that is tailored to handling and processing of patient-derived materials.

3. The work station of claim 1 further comprising a work surface that slides to expose a space for the storage of tools.

4. The work station of claim 1, further comprising instrumentation to perform on-site analysis of the fluids at the work station.

5. The work station of claim 1, wherein the work station is a closed system that permits on-site processing of the patient sample.

6. The work station of claim 1, further comprising angular-shaped side panels disposed on each side of the work station to permit entrance into the work station from each side of the work station.

* * * * *